United States Patent [19]

Prange et al.

[11] 4,399,300
[45] Aug. 16, 1983

[54] METHOD OF PREPARING MALONIC ACID DIALKYL ESTERS

[75] Inventors: Uwe Prange, Niederkassel-Ranzel; Moustafa El Chahawi, Troisdorf; Wilhelm Vogt, Cologne; Hermann Richtzenhain, Much-Schwellenbach, all of Fed. Rep. of Germany

[73] Assignee: Dynamit Nobel Aktiengesellschaft, Troisdorf, Fed. Rep. of Germany

[21] Appl. No.: 260,444

[22] Filed: May 4, 1981

Related U.S. Application Data

[63] Continuation of Ser. No. 169,009, Jul. 15, 1980, abandoned, which is a continuation of Ser. No. 879,993, Feb. 28, 1978, abandoned, which is a continuation of Ser. No. 687,841, May 19, 1976, abandoned.

[30] Foreign Application Priority Data

Jun. 2, 1975 [DE] Fed. Rep. of Germany ....... 2524389
Jan. 28, 1976 [DE] Fed. Rep. of Germany ....... 2603026

[51] Int. Cl.$^3$ ............................................. C07C 67/36
[52] U.S. Cl. .............................. 560/204; 252/431 R; 560/190
[58] Field of Search ..................... 560/204; 252/431 R

[56] References Cited

U.S. PATENT DOCUMENTS

3,116,306 12/1963 Heck .................................. 560/105
3,974,202 8/1976 El Chahawi et al. .............. 560/105
4,128,572 12/1978 Cassar ................................ 560/406

FOREIGN PATENT DOCUMENTS

2240398 2/1974 Fed. Rep. of Germany ...... 560/204
2240399 2/1974 Fed. Rep. of Germany ...... 560/204
2359963 6/1975 Fed. Rep. of Germany ...... 560/204

OTHER PUBLICATIONS

Sidgwick, *Chemical Elements and Their Compounds*, p. 1422, vol. II, (1950).
Cotton, *Advanced Inorganic Chemistry*, pp. 702–703, 3rd Ed., (1972).

*Primary Examiner*—Natalie Trousof
*Assistant Examiner*—Vera C. Clarke
*Attorney, Agent, or Firm*—Felfe & Lynch

[57] ABSTRACT

Production of malonic acid dialkyl esters by reacting halogen acetic acid alkyl ester with carbon monoxide, and alkali alcoholate, alkali earth alcoholate or a solution of alkali hydroxide in an alcohol at a pH of up to 8.5 in the presence of a cobalt compound which is a catalyst for the reaction.

12 Claims, No Drawings

METHOD OF PREPARING MALONIC ACID DIALKYL ESTERS

This application is a continuation of Ser. No. 169,009, filed July 15, 1980, now abandoned, which is a continuation of Ser. No. 879,993, filed Feb. 28, 1978, now abandoned, which is a continuation of Ser. No. 687,841, filed May 19, 1976, now abandoned.

BACKGROUND

The present invention relates to a method of preparing malonic acid dialkyl esters by the reaction of halogen acetic acid alkyl esters with carbon monoxide and alkali alcoholates or alkaline earth alcoholates in the presence of a catalyst containing a cobalt compound and of an alcohol on which the alcoholate is based as a solvent.

Alkali hydroxides dissolved in the alcohols can be used instead of the alcoholates.

A known method for preparing malonic acid dialkyl esters consists in the reaction of chloroacetic acid with alkali cyanide to produce cyanacetic acid, saponification of the nitrile, and then esterification to the diester (Ullmann 1960, vol. 12, p. 192). What is unsatisfactory about this method is the plurality of steps involved in the reaction, and the use of cyanides whose toxicity creates problems not only in handling them but also in getting rid of their residues without contaminating the environment.

In addition, malonic acid dialkyl ester can be obtained by setting out from chloroacetic acid ester with stoichiometric amounts of $Na[Co(CO)_4]$ with the formation of cobalt carbonyl hydride as an intermediate, and the decomposition of the latter (R. F. Heck and D. S. Breslow, J. Amer. Chem. Soc., 85, 2779–82 (1963)). The yield in this reaction, however, is low.

In a number of publications the carboxylation of acetic acid alkyl esters in the presence of phenolates in aprotic solvents is also described (G. Bottacio, G. P. Chiusoli and M. G. Felicioli, Gazz. Chim. Ital. 103, 105 (1973) and German Offenlegungsschrift 2,038,725). However, unsatisfactory yields and the complicated processing of the reaction product are obstacles to the technical application of these reactions. Herein phenolate can be absent. Aprotic solvents can also be absent.

Another known method is based on the carbonylation of chloroacetic acid alkyl esters with carbon monoxide in an alcohol in the presence of $Co_2(CO)_8$ or iron carbonyl and basic substances such as carbonates, bicarbonates, acetates and secondary and tertiary phosphates of the alkali metals as well as oxides of the alkaline earth metals such as MgO and CaO or tertiary amines, on the condition that, with these compounds, there will be no further reaction between the malonic ester that forms and the halogen acetic esters, but this is accomplished only in the case of weakly basic substances. Disadvantages of this process consist in the fact that water is formed in the reaction, which permits the alcohol to be reused only after removal of the water, in the very high catalyst concentration and the high pressures, and, if carbonates or bicarbonates are used, in the formation of carbon dioxide which reduces the partial pressure of the carbon monoxide used and therefore requires apparatus that can withstand high pressures. See U.S. application Ser. No. 527,798, filed Nov. 27, 1974 (Group Art Unit 127). Herein water and the weakly basic substances can be absent.

THE INVENTION

It has been found that malonic acid dialkyl esters can be produced in an unexpected manner by the carbonylation of halogen acetic acid alkyl esters at carbon monoxide pressures of 1 to 30 atmospheres absolute, in the presence of a cobalt catalyst with alkali or alkaline earth alcoholates, without the formation of $H_2O$ in the reaction and without the need for a carbon dioxide washing of the carbon monoxide before recycling the latter. There is no pollution of the environment by harmful substances.

Contrary to expectations, therefore, the known reactions of chloroacetic ester and alkali alcoholate as well as malonic ester with alcoholate and chloroacetic ester do not take place.

For example, if chloroacetic acid ethyl ester is made to react with sodium ethylate, ethoxyacetic acid ethyl ester will be formed in good yields (Scheibler, Marhenkel and Nikilic, Ann. 458, 36 (1927), and if chloroacetic acid ethyl ester is made to act on malonic acid diethyl ester in the presence of sodium ethylate, carboxysuccinic acid triethyl ester and $\beta$-carboxytricarballylic acid tetraethyl ester are formed (Bischoff, Ber. 29, 966 (1896). Therefore it is surprising that malonic acid dialkyl ester is formed in very good yields from halogen acetic acid alkyl esters, a solution of an alkali alcoholate or alkaline earth alcoholate in the alcohol that is the basis of the alcoholate, and carbon monoxide, in the presence of catalytic amounts of a cobalt catalyst. This can be achieved if, preferably, the alcoholate solution or alkali hydroxide in alcohol, is proportioned into the reaction mixture in such a manner that a pH of 8.5 or less is maintained. Since the pH is measured in a nonaqueous solution, the pH values indicated by the pH meter do not have to agree with the actual pH values measurable in aqueous solutions and defined on the basis of aqueous solutions. At the same time, the formation of alkoxyacetic acid alkyl esters can be completely prevented.

It is to be understood that pH meter readings are to be generally between about 3 and 8.5 or up to about 8.7 maximum, preferably between 4 and 8.5, and more preferably between 5 and 8.5, a lower pH of, say, 1 to 2 being allowed to occur only briefly if at all, during the reaction.

The subject matter of the invention is therefore a method of preparing malonic acid dialkyl esters by the reaction of halogen acetic acid alkyl esters with carbon monoxide in the presence of a catalyst containing a cobalt compound, characterized in that the reaction is performed with an alkali alcoholate or alkaline earth alcoholate or with a solution of alkali hydroxide in an alcohol at a pH of 8.5 or less. The halogen acetic acid alkyl ester corresponds to the malonic acid dialkyl ester produced.

The reaction takes place according to the equation:

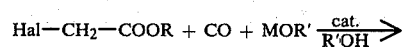

R'OCC—CH$_2$—COOR + MHal

In the reaction equation, R and R' represent primary, secondary or tertiary alkyl groups of 1 to 8 carbon atoms, and can be different or identical radicals or groups, Hal represents preferably chlorine or, in some cases, bromine or iodine, and M represents preferably sodium or potassium or, in some cases, $Mg/2$ or Li.

The alkali hydroxides are particularly NaOH, but they can also be KOH or LiOH, concentrated solutions thereof in the alcohol being desirable.

By the present invention malonic esters are obtainable in a very economical manner in a one-step process, the alcohol used as solvent can be recycled, and the excess carbon monoxide can be reused without expensive carbon dioxide washing. Furthermore, in contrast to the conventional cyanide method, the difficult removal of cyanide residues is obviated, thereby preventing the endangerment of the environment.

The reaction is performed by heating an alcoholic solution of the catalyst together with the halogen acetic acid alkyl ester to the reaction temperature at a pH of 8.5 or less, or else the halogen acetic acid alkyl ester is added rapidly after reaching the reaction temperature. Then the alcoholic solution of the alkali or alkaline earth alcoholate is proportioned into the mixture, with thorough mixing of the gas phase and the liquid phase, at such a rate that the pH drops below a certain specified level, which is to be 8.5 or less. During the reaction a constant carbon monoxide pressure is sustained. The amount of the alkali alcoholate or alkaline earth alcoholate is governed according to the transformation of the halogen acetic acid alkyl ester, and upon the complete transformation it will be one mole of an alkali alcoholate or 0.5 mole of an alkaline earth alcoholate per mole of halogen acetic acid alkyl ester.

Suitable alcoholates are lithium, potassium and magnesium alcoholates. They are generally used in the form of highly concentrated solutions in the same alcohol from which the alcoholate is formed.

Primary, secondary or tertiary alcohols having 1 to 8 carbon atoms are used as the alcohols, examples being methanol, ethanol, propanol, isopropanol, n-butanol, sec. butanol, isobutanol, tert. butanol, or 2-ethylhexanol.

The reaction of the above-named reactants is performed in the temperature range from 0° C. to 150° C., preferably between 20° C. and 80° C. The reaction time is from two to ten hours, depending on the selected temperature, the carbon monoxide pressure and the catalyst concentration.

The reaction of the halogen acetic acid esters takes place at a carbon monoxide pressure of as little as 0.1 atmospheres absolute. Higher pressures up to 30 at. abs. and more are possible, but not necessary or desirable. Preferably the reaction is performed at pressures between 0.5 and 20 at. abs. 1.2 to 10 at. abs. is sufficient even for the achievement of high yields.

The catalyst can be a cobalt compound such as $Co_2(CO)_8$ or a catalyst system consisting of cobalt salts, such as for example cobalt halide, cobalt acetyl acetonate, cobalt acetate, cobalt nitrate, basic cobalt carbonate or cobalt naphthenate together with manganese powder and sodium dithionite ($Na_2S_2O_4$). The molar ratio of cobalt compound to halogen acetic acid alkyl ester can be between 1:5 and 1:1000, preferably between 1:15 and 1:200.

The molar ratio of the cobalt compound to the manganese powder or manganese alloy can be from about 1:1 to about 1:0.1. The proportion of the dithionite is smaller, the molar ratio of the cobalt compound to the dithionite being generally from 1:0.4 to 1:0.05. In special cases, however, the quantity ratios can be different.

Starting materials for the malonic acid dialkyl esters are monohalogen acetic acid alkyl esters, such as chloro-, bromo- or iodo-acetic acid alkyl esters. The chloroacetic acid esters are preferred on account of their easy availability.

The malonic acid alkyl esters prepared by the method of the invention are known to be valuable chemical intermediate products, for the preparation of pharmaceuticals.

EXAMPLES

In the following examples of embodiments of the invention, the percentages stated are percentages by weight, unless otherwise specified, and the pressures are given in atmospheres gauge.

EXAMPLE 1

In a pressure vessel of a capacity of 7.5 liters, equipped with a pH measuring system, 20 g of $Co_2(CO)_8$, 10 g of NaCl as conducting salt, and 2.5 liters of ethanol denatured with toluene are combined. The apparatus is scavenged three times with carbon monoxide, and then a CO pressure of 7.5 atmospheres gauge is established. While the vessel is heated at 55° C., a solution of 20.5% sodium ethylate in ethanol is pumped in from a reservoir by means of a proportioning pump such that a pH of 7 to 8 is reached, the liquid and gas phases being thoroughly mixed by means of a circulating pump. After the reaction temperature is reached, 490 g (4 moles) Of chloroacetic acid ethyl ester is proportioned into the vessel at a constant CO pressure of 8.0 at. gauge over a period of 15 minutes, and a 20.6% solution of sodium ethylate is added through a second inlet so as to maintain a pH of approximately 7.0. Over a period of 6 hours, 1.12 kg (3.4 moles) of 20.6% sodium ethylate is pumped in. Then the vessel is cooled, the pressure is relieved, and the vessel is purged with nitrogen. The reaction solution is separated from the sodium chloride on a suction filter and distilled. 517 g of malonic acid diethyl ester is obtained (95% yield), plus 2.5 g of acetic acid ethyl ester (approx. 1% yield) and 5 g of high-boiling compounds plus 73 g of chloroacetic acid ethyl ester.

EXAMPLE 2

As in Example 1, but with 25 g of $Co_2(CO)_8$ and 2.5 l of methanol, at 5.2 at. CO and 60° C., 868 g (8 moles) of chloroacetic acid methyl ester is reacted for 5½ hours at a pH of approximately 8.0 with 1.67 kilograms of 17.8% sodium methylate (5.5 moles) in methanol. After processing, 660 g of malonic acid dimethyl ester is obtained (yield 91%) plus 22 g of acetic acid methyl ester (yield 5.5%) and about 20 g of high-boiling compounds, and 271 g of chloroacetic acid methyl ester.

EXAMPLE 3

As in Example 1, but at 7.5 at. CO and a pH of 6.0, 490 g (4 moles) of chloroacetic acid ethyl ester is reacted with 1.38 kg of 15.8% sodium ethylate (3.2 moles) in ethanol, for 6 hours. Processing the reaction mixture yields 490 g of malonic acid diethyl ester (95% yield), 4.4 g of acetic acid ethyl ester (1.6% yield), 5.9 g of residue, and 98 g of chloroacetic acid ethyl ester.

EXAMPLE 4

As described in Example 1, but with 160 g of an 8.85% solution of $Co_2(CO)_8$ in ethanol, 2.7 moles out of 4 moles of chloroacetic acid ethyl ester are reacted at 7.5 at. CO and 55° C. in 5¼ hours. 400 g of malonic acid diethyl ester is obtained (93% yield) and 3.5 g of acetic acid ethyl ester plus 160 g of chloroacetic acid ethyl ester.

EXAMPLE 5

As in Example 1, but in a pressure vessel with a capacity of 18 liters equipped with a pH measuring system, 3.06 kg (25 moles) of chloroacetic acid ethyl ester, 1 liter of ethanol and 125 g of $Co_2(CO)_8$ are combined at 5 at. CO. At a reaction temperature of 55° C., 7.03 kg of 21.9% sodium ethylate (22.6 moles) is pumped in over a period of 5½ hours, at a pH of 7.0. 3.43 kg of malonic acid diethyl ester is obtained (yield 95%) plus 290 g of chloroacetic acid ethyl ester.

EXAMPLE 6

In a one-liter glass flask equipped with stirrer, 2 dropping funnels, a reflux condenser, a glass electrode and a glass inlet tube for carbon monoxide, 108.5 g (1 mole) of chloroacetic acid methyl ester is reacted for 6½ hours with 1 mole of potassium methylate (28.75% solution in methanol) in the presence of 10 g of $Co_2(CO)_8$, at 70° C., 0.8 at. CO, and a pH of approximately 8.5. The processing yields 119 g of malonic acid dimethyl ester (90% yield), and small amounts of acetic acid methyl ester and methoxyacetic acid methyl ester, plus 5 g of higher-boiling substances.

EXAMPLE 7

In the apparatus described in Example 6, 122.5 g of chloroacetic acid ethyl ester is reacted with 1 mole of sodium ethylate for 6 hours at 0.5 at. CO, 55° C. and a pH of 7.0, but instead of $Co_2(CO)_8$, the catalyst is 8 g of $CoCl_2.6H_2O$, 5 g of manganese powder and 1 g of $Na_2S_2O_4$. Processing yields 136 g of malonic acid diethyl ester (yield 85%) plus 12 g of higher-boiling substances.

EXAMPLE 8

If Example 7 is repeated using ½ mole of magnesium ethylate instead of sodium ethylate, the reaction and the yield are found to be similar.

EXAMPLE 9

In a pressure vessel with a capacity of 7.5 liters, there are combined 20 g of $Co_2(CO)_8$ in 2.5 liters of ethanol, and 612.5 g (5 moles) of chloroacetic acid ethyl ester, in a nitrogen atmosphere. Then the apparatus is scavenged three times with carbon monoxide, and a CO pressure of 7 bars is established. After the reaction temperature of 55° C. is reached, an 11.8% ethanolic solution of NaOH is pumped in by a proportioning pump at a CO pressure of 8 bars, in such a manner that a pH value of about 7.0 is sustained during the reaction. The reaction solution is constantly agitated during the reaction by means of a circulation pump. After 5 hours of reaction time a transformation of 79.2% is achieved. The reaction solution is separated from the NaCl on a rotary evaporator and distilled. 596 grams of malonic acid diethyl ester (94% yield) are obtained, and 20 g of acetic acid ethyl ester (5.7% yield) plus 127 g of chloroacetic acid ethyl ester.

EXAMPLE 10

By the procedure of Example 1, but using 20 g of $Co_2(CO)_8$ in 2.5 liters of $CH_3OH$ and using 542.5 (5 moles) of chloroacetic acid methyl ester and a 22.2% methanolic solution of sodium hydroxide, a transformation of 72% is achieved after 5 hours of reaction time at a pH of 7.0. After processing, 477 g of malonic acid dimethyl ester is obtained (87% yield), plus 32 g of acetic acid methyl ester (12% yield) and 150 g of chloroacetic acid methyl ester.

EXAMPLE 11

20 g of $Co_2(CO)_8$ in 2.5 liters of isopropanol and 546 g (4 moles) of chloroacetic acid isopropyl ester are placed in a pressure vessel of a capacity of 18 liters, as in Example 1. At 55° C., and a pressure of 5 bars of CO, a 2.93% solution of sodium hydroxide in isopropanol is pumped into the vessel over a period of 3 hours, maintaining a pH of 7.0. At a transformation of 82%, 615 g of malonic acid diisopropyl ester (92% yield) is obtained after the usual processing. 98 g of chloroacetic acid isopropyl ester is recovered.

What is claimed is:

1. Process for producing malonic acid dialkyl ester which consists essentially of contacting the corresponding halogen acetic acid alkyl ester wherein said halogen is chlorine, bromine or iodine with carbon monoxide, an alkylol of 1–8 carbon atoms, and alkali alcoholate, alkali earth alcoholate or a solution of alkali hydroxide in said alkylol, said alcoholate moiety corresponding to said alkylol, at a pH of up to 8.5 in the presence of $Co_2(CO)_8$ as catalyst for the reaction, at a temperature of 0° C. to 150° C. and a carbon monoxide pressure of 0.1–50 atmospheres absolute.

2. Process of claim 1, wherein the catalyst is $Co_2(CO)_8$ and the catalyst and halogen acetic acid alkyl ester are in a molar ratio of cobalt compound to halogen acetic acid alkyl ester of 1:5 to 1:1000.

3. Process of claim 1, wherein the cobalt catalyst and halogen acetic acid alkyl ester are in a molar ratio of cobalt compound to halogen acetic acid alkyl ester of 1:15 to 1:200.

4. Process of claim 1, wherein the alkali or alkali earth is lithium, sodium, potassium or magnesium.

5. Process of claim 1, wherein alcoholate is employed and the alcoholate is in a solution in the alcohol on which the alcoholate is based.

6. Process of claim 1, wherein the alkali alcoholate or alkali earth alcoholate or alkali hydroxide in alcohol is proportioned so that the pH is up to 8.5.

7. Process of claim 1, wherein alkali alcoholate or alkali earth alcoholate is employed and the alkali alcoholate or alkaline earth alcoholate is proportioned so that the pH is up to 8.5.

8. Process of claim 1, wherein the contacting is performed in the temperature range from 20° C. to 80° C.

9. Process of claim 1, wherein the contacting is performed at a carbon monoxide pressure of 0.5–20 atmospheres absolute.

10. Process of claim 1, wherein:
    (a) the alkali or alkali earth is lithium, sodium, potassium or magnesium,
    (b) the alcohol moiety of the alcoholate or the alcohol is of or is, a primary, secondary or tertiary alcohol having 1 to 8 carbon atoms,
    (c) the contacting is performed in the temperature range from 0° C. to 150° C.,
    (d) the contacting is performed at a carbon monoxide pressure of 0.1–50 atmospheres absolute.

11. Process of claim 10, wherein the cobalt catalyst and halogen acetic acid alkyl ester are in a molar ratio of cobalt compound to halogen acetic acid alkyl ester of 1:5 to 1:1000.

12. Process of claim 11, wherein the alcoholate is employed and the alcoholate is in a solution in the alcohol in which the alcoholate is based.

* * * * *